United States Patent
Link et al.

(10) Patent No.: US 12,115,277 B2
(45) Date of Patent: Oct. 15, 2024

(54) ANTI-MICROBIAL IMPLANT COATING

(71) Applicant: Waldemar Link GmbH & Co. KG, Hamburg (DE)

(72) Inventors: Helmut D. Link, Hamburg (DE); Richard Csaszar, Bad Segeberg (DE)

(*) Notice: Subject to any disclaimer, the term of this patent is extended or adjusted under 35 U.S.C. 154(b) by 886 days.

(21) Appl. No.: 17/053,480

(22) PCT Filed: Apr. 30, 2019

(86) PCT No.: PCT/EP2019/061011
§ 371 (c)(1),
(2) Date: Nov. 6, 2020

(87) PCT Pub. No.: WO2019/214992
PCT Pub. Date: Nov. 14, 2019

(65) Prior Publication Data
US 2021/0128782 A1    May 6, 2021

(30) Foreign Application Priority Data

May 7, 2018 (EP) ..................... 18171026

(51) Int. Cl.
| | | |
|---|---|---|
| A61L 27/30 | (2006.01) | |
| A61L 27/04 | (2006.01) | |
| A61L 27/06 | (2006.01) | |
| A61L 27/10 | (2006.01) | |
| A61L 27/54 | (2006.01) | |
| C23C 14/02 | (2006.01) | |
| C23C 14/06 | (2006.01) | |
| C23C 14/26 | (2006.01) | |

(52) U.S. Cl.
CPC ........... *A61L 27/306* (2013.01); *A61L 27/047* (2013.01); *A61L 27/06* (2013.01); *A61L 27/10* (2013.01); *A61L 27/54* (2013.01); *C23C 14/022* (2013.01); *C23C 14/0641* (2013.01); *C23C 14/26* (2013.01); *A61L 2300/104* (2013.01); *A61L 2300/404* (2013.01); *A61L 2300/606* (2013.01); *A61L 2420/02* (2013.01); *A61L 2420/06* (2013.01); *A61L 2430/38* (2013.01)

(58) Field of Classification Search
CPC .... A61L 27/06; A61L 27/10; A61L 2300/104; A61L 2300/606
See application file for complete search history.

(56) References Cited

U.S. PATENT DOCUMENTS

| | | | |
|---|---|---|---|
| 2009/0198343 A1 | 8/2009 | Spain et al. | |
| 2012/0083898 A1 | 4/2012 | Thull et al. | |
| 2016/0106541 A1* | 4/2016 | Thull | A61L 27/06 623/18.11 |
| 2020/0276019 A1* | 9/2020 | Shetty | B33Y 40/20 |

FOREIGN PATENT DOCUMENTS

| | | |
|---|---|---|
| CN | 106175996 A | 12/2016 |
| DE | 2647088 A1 | 4/1978 |
| EP | 2444108 A1 | 4/2012 |
| WO | WO 2009/094684 A2 | 8/2009 |

OTHER PUBLICATIONS

Machado, D. et al. "Structural and Morphological Changes in Ag:TiN Nanocomposite Films promoted by in-vacuum annealing" Journal of Nano Research vol. 25 (2013) pp. 67-76 (Year: 2013).*
Claus Moseke et al., "Hard implant coatings with antimicrobial properties," Journal of Materials Science: Materials in Medicine, Kluwer Academic Publishers, BO, vol. 22, No. 12, Oct. 16, 2011 (Oct. 16, 2011), pp. 2711-2720, XP019985467.
Thomson Scientific, London, GB; vol. 2017, No. 17, AN 2017-00457E, abstract No. 0, XP002786273.
T De Los Arcos et al., "Preparation and characterization of TiN—Ag nanocomposite films," Vacuum., GB, vol. 67, No. 3-4, Sep. 1, 2002, (Sep. 1, 2002), pp. 463-470, XP055353364.
International Search Report and Written Opinion mailed Jul. 19, 2019 in corresponding International Application No. PCT/EP2019/061011.
Yunqing, "Atlas of the Human Body Anatomy, Histology Pathology", Henan Science and Technology Press, 2012, 8 pgs (including translation).
Jiquan et al., "Introduction to 3D Printing Technology", Nanjing Normal University Press, 2016, 6 pgs (including translation).
Randhawa, "Coatings Technology Handbook", China Petrochemical Press, 2003, 7 pgs (including translation).
Warren et al., "Selected Papers of the Third International Conference on Thermal Treatment of Materials", Society of Thermal Treatment of Chinese Mechanical Engineering Society, Machinery Industry Press, 1985, 3 pgs. (including translation).
"Sample Preparation Techniques in Analytical Chemistry", Mithra, (USA), People's Public Security University Press of China, 2015, 9 pgs (including translation).
Notification of the Second Office Action mailed Jun. 14, 2022, in connection with Chinese Patent Application No. 201980031027.8, filed Nov. 6, 2020, 17 pgs (including translation).
Notification of the First Office Action mailed Dec. 15, 2021, in connection with Chinese Patent Application No. 201980031027.8, filed Nov. 6, 2020, 18 pgs. (Including Translation).

* cited by examiner

*Primary Examiner* — Andrew S Rosenthal
(74) *Attorney, Agent, or Firm* — Chiesa Shahinian & Giantomasi PC

(57) ABSTRACT

A coating for an implant component, in particular a component of a spinal implant, is provided. The coating is a ceramic titanium nitride coating comprising an at % content of 5 to 30 At % of Ag in addition to an at % content of Ti and an at % content of N.

20 Claims, No Drawings

ANTI-MICROBIAL IMPLANT COATING

CROSS-REFERENCE TO RELATED APPLICATIONS

This application is the National Stage entry under 35 U.S.C. § 371 of International Application No. PCT/EP2019/061011 filed on Apr. 30, 2019, published on Nov. 14, 2019 under Publication Number WO 2019/214992 A1, which claims the benefit of priority under 35 U.S.C. § 119 of European Patent Application Number 18171026.0 filed on May 7, 2018, the entireties of which are herein incorporated by reference.

FIELD OF THE INVENTION

The invention relates to a coating for implants, a method for applying this coating as well as a use of this coating on an implant.

PRIOR ART

One of the reasons for the failure of an implant in situ is an infection with pathogens. Pathogens that can cause such failure are, in particular, staphylococci, such as *Staphylococcus epidermidis*. They colonise the skin and mucosas of a human being. Inter alia the pathogen *Staphylococcus epidermidis* furthermore has, for example, the ability to colonise on an implant surface by means of a biofilm. In this biofilm, this pathogen is protected against antibiotics, phagocytes and other immune responses of the body. There is evidence that *Staphylococcus epidermidis* is a common cause of postoperative infections following the implantation of implants.

If such an infection is detected, an attempt is generally made to suppress it with active substances such as antibiotics. However, if this course of action is not successful, it may be necessary to remove the implant again. At least part of the source of infection is removed by removing the implant. Although this course of action leads to an easier treatment of the infection, it also results in a reduced mobility of the patient.

In the case of an infection with *Staphylococcus epidermidis*, matters are furthermore complicated by the fact that this germ often displays resistance to antibiotics (80% according to Takizawa et al. in SPINE, Volume 42, No. 7, pages 525 to 530). According to Takizawa, there are indications in the field of spinal surgery that the pathogens known as methicillin-resistant *Staphylococcus epidermidis* (MRSE) show fewer signs of infection due to their lower virulence and thus give rise to the risk of an infection only being detected at a late stage. In the worst case, this can lead to higher morbidity for a patient postoperatively than preoperatively, in particular if the use of an implant is no longer possible owing to the infection.

In order to avoid such complications, it is therefore desirable to already counteract the colonisation of pathogens. For example, US 2009/0198343 A1 proposes to provide a coating for an artificial joint, intended for the running surfaces of metal pairings, with an antimicrobial effect. In order to achieve this, a chromium nitride coating is supplemented by silver in US 2009/0198343 A1 by alternately coating the friction surface of the implant with chromium nitride and silver. However, chromium nitride is classified as sensitising, and there is thus a risk of allergic reactions occurring after implantation. In addition, the coating disclosed in US 2009/0198343 A1 only has a very limited effect against a colonisation of *Staphylococcus epidermidis*.

SUMMARY OF THE INVENTION

The object of the present invention was therefore to provide a coating for an implant surface that prevents an infection in situ. The object of the invention was in particular to provide a coating for an implant surface that counteracts the colonisation of pathogens, in particular *Staphylococcus epidermidis*. It was also the aim that the coated implant surface should not cause allergies or hypersensitivity in the patient. The coated implant surface should furthermore be able to withstand any mechanical influences that may occur in particular during the surgical procedure of implantation.

In order to solve these objects, a coating is provided according to claim 1, a method for applying this coating is provided according to claim 10 and a use of this coating on an implant is provided according to claim 12.

The invention thus provides a coating for an implant component, in particular a component of a spinal implant, said coating being a ceramic titanium nitride coating having an at % content of 5 to 30 at % of Ag in addition to an at % content of Ti and an at % content of N.

Such a content of silver can prevent an infection caused by pathogens. An antimicrobial effect against *Staphylococcus epidermidis* has in particular been found.

Furthermore, the At % content of Ag, i.e. the silver content, can at the same time be kept so low that the mechanical resistance of the coating is sufficient for the mechanical contact forces occurring during implantation. In other words, the coating of the implant is not damaged during implantation. This is especially true when inserting the coated implant into bone tissue or when screwing the implant into bone tissue. It is presumed that the mechanical resistance remains at such a level since, even though the silver content reduces the hardness of the coating, it increases the ductility of the coating. The implant material located underneath the coating or the base material of the implant can thus be prevented from coming into contact with the body tissue of a patient, possibly causing hypersensitivity.

Owing to its resistance, the ceramic titanium nitride coating with a silver content, i.e. the titanium nitride/silver coating, is particularly suitable for structural implants that support or replace parts of the skeleton when they have been introduced into the body of a patient. Even though the coating is particularly advantageous for spinal implants, it can therefore also be advantageously used for other implant components, in particular structural implants. These include, for example, an implant component of a joint endoprosthesis or bone implants that replace at least part of a bone.

In a preferred embodiment, the coating comprises 5 to 20 at % of Ag, 8 to 15 at % of Ag, 8 to 10 at % of Ag or approximately 10 at % of Ag.

These preferred silver contents in the coating meet the above requirements. With regard to hardness, it is the case that the lower the silver content, the higher the hardness. However, as described above, a reduction in hardness does not significantly affect the resistance of the coating for implantation of the coated implant.

In a particularly preferred embodiment, silver and titanium nitride are formed or arranged adjacent to one another on the coating surface.

This allows the Ag content to display its infection-inhibiting effect. In order to achieve this adjacent structure of the coating on the surface and thus direct contact with the tissue or fluids of the patient, the two coating components are applied at least partially at the same time. Owing to this simultaneous application, the coating components are furthermore essentially distributed evenly on the surface of the implant.

In another preferred embodiment of the coating, it has a thickness of 2.5 to 6 μm, 3.5 to 5.5 μm or approximately 4.5 μm.

It was found that at these coating thicknesses, at least partial destruction of the coating is prevented. A thicker coating tends to be advantageous, in particular if the silver content in the coating layer is in the upper part of the aforementioned ranges. However, a thickness exceeding these values does not lead to any significant improvements and may even encourage inhomogeneity and delamination of the coating. It is presumed that the mechanical resistance of the coating at the specified thicknesses is also due to the fact that no continuous sections of silver are formed in the thickness direction. In other words, owing to the three-dimensional heterogeneous structure of the titanium nitride/silver coating, there is an in principle continuous titanium nitride coating.

In a further preferred embodiment, the titanium nitride coating is essentially a stoichiometric TiN layer.

Together with the silver content, such a layer forms a particularly uniform inert layer with an antimicrobial effect and thus prevents both hypersensitivity and infection after implantation of the implant.

Furthermore, the present invention provides at least one implant component, in particular of a spinal implant, which is coated at least in sections with a coating according to one of the preceding claims.

As described above, infections can occur in particular owing to implants exposed to the environment before implantation. It was thereby found that in particular in the spinal region, such infections are due to the pathogen *Staphylococcus epidermidis*. For this reason, the preventive effect of a coating according to the invention is particularly effective here.

It must be emphasised that even damage to the coating has very little, if any, impact on the infection-inhibiting effect of the coating.

In a preferred embodiment, the implant component is at least one component of a spondylodesis implant or a spinal cage.

In the case of a spondylodesis implant, all parts, such as connecting elements, rods and screws, are preferably provided with the present coating. Cages are also highly suitable for the use of this coating since they often have a complex and angled geometry. Spinal cages can furthermore comprise anchoring elements that engage with the bone tissue of the vertebral bodies and are loaded accordingly when such a spinal cage is inserted between two vertebral bodies.

In a further particularly preferred embodiment, the surface of the coated section of the implant component comprises titanium nitride with Ag islands or silver islands embedded therein.

As described above, such a distribution of titanium nitride and silver in the coating can provide an essentially continuous titanium nitride coating. As a result, a sufficient mechanical resistance of such a coating is achieved.

In a further embodiment, the implant component to be coated comprises a titanium alloy and consists preferably thereof.

On the one hand, owing to the titanium nitride content, the titanium nitride/silver coating adheres particularly well to a titanium alloy of such an implant component and thus prevents damage to the coating caused by detachment. On the other hand, an implant component to be coated that is made of a titanium alloy reduces the risk of hypersensitivity even further since such hypersensitivity is unlikely even if the coating is damaged owing to the biocompatibility of titanium.

The present invention furthermore provides a method for applying a coating to an implant component, which comprises the steps of providing an implant component to be coated, in particular an implant component for a spinal implant, in a coating chamber, providing at least one target having an At % content of silver and titanium that is predetermined for the coating, and/or providing at least one Ti target and at least one Ag target, and evaporating the at least one target in an atmosphere containing at least nitrogen, and simultaneously coating the implant component with the evaporated metal of the at least one target.

This method allows a simultaneous coating with titanium nitride and silver to form the titanium nitride/silver coating. Simultaneous coating ensures that silver is exposed on the surface of the coating and that the infection-inhibiting effect of the coating can thus unfold. Furthermore, by selecting the number of the respective targets of the coating components, the at % content can be adjusted at least in its order of magnitude to the desired composition of the coating.

As an alternative or in addition to adjusting the composition of the coating via the number of respective targets, at least one target having a predetermined ratio of titanium and silver can be provided. Preferably used, however, is only one or more such targets with at % contents of titanium and silver predetermined according to the desired composition of the coating.

In a preferred embodiment of the method, the evaporation of the at least one target is carried out by arc evaporation, the voltage applied to the targets being 15 to 30 V or 20 to 25 V, and the applied current being 40 to 70 A.

These adjustment ranges of the voltage and the current, like the number of targets of the respective coating component mentioned above, allow the coating composition to be adjusted. In particular a finer adjustment can thereby be achieved than with the selection of the number of targets.

In a further embodiment of the method, once the implant to be coated has been provided in the coating chamber, the implant surface to be coated is cleaned by a glow discharge under a hydrogen atmosphere.

This cleaning step has the advantage that any organic residues present on the surface of the implant to be coated are removed, thus improving the adhesion of the coating to the implant.

In a further preferred embodiment of the method, once the implant to be coated has been introduced into the coating chamber, the implant surface to be coated is cleaned by bombarding the implant surface with ions under an inert atmosphere.

This removes a possibly existing oxide layer on the implant surface, which would otherwise reduce the adhesion of the coating to the implant.

Such an oxide layer is formed, for example, in implants made of titanium alloys and can be removed in particular by bombarding them with titanium ions using the method step of this embodiment. The titanium ions can thereby preferably be generated via a Ti target to be used for the coating. The inert atmosphere, such as an argon atmosphere, thereby counteracts the formation of a new oxide layer.

The invention furthermore provides a use of the coating for preventing a biofilm on an implant, in particular a spinal implant.

Such a use of the coating is, as described above, particularly advantageous.

DETAILED DESCRIPTION OF PREFERRED EMBODIMENTS

In the context of the present invention, a coating is to be understood as a coating applied by a technical process. Examples of such technical processes are chemical vapor deposition (CVD), physical vapor deposition (PVD) or electroplating.

As described above, a coating according to the invention comprises a mixture of titanium nitride and silver, also referred to herein as a titanium nitride/silver coating. In other words, the coating comprises at least one single layer of a ceramic titanium nitride coating, in which silver is embedded. The silver is present in the form of silver islands, i.e. silver or silver atoms are arranged next to the titanium nitride lattice. Owing to the size of the silver atoms, it is assumed that only a small proportion, if any, of the silver is arranged interstitially in the titanium nitride lattice. It was instead observed that the silver is present in the form of silver agglomerates in the titanium nitride/silver coating. In other words, the silver is present in the titanium nitride lattice but is not integrated therein. These silver agglomerates are preferably present in a range of 1 µm to 50 µm and even more preferably in a range of 5 µm to 30 µm.

It is furthermore assumed that the effectiveness of the silver is due in particular to the fact that in the implanted state of the implant, the silver transforms via local element formation into the ionic state upon contact with body fluid and thus develops its antimicrobial effect. That this local element formation can take place is made possible by an arrangement of these islands on the surface of the coating. This arrangement is achieved by an at least partially simultaneous coating of the implant with titanium nitride and silver.

Owing to its antimicrobial properties, the coating has an infection-inhibiting effect, which particularly applies to *Staphylococcus epidermidis*. It is presumed that the silver content of the coating present in the titanium nitride matrix disrupts the formation of a biofilm that these bacteria develop. As a result of this disruption, the protective mechanism of the bacteria against antibiotics that is generated by this biofilm at least no longer functions adequately.

It was furthermore observed that the silver can dissolve out of the coating in ion form. It is assumed that these silver particles ionised on the surface of the coating form an effect zone (inhibition zone) in the immediate vicinity of the implant, in which they display an antimicrobial effect. Consequently, not only an infection spreading directly from the surface of the implant can be prevented by the coating.

A titanium nitride/silver coating with a silver content of 5 to 30 At-% displays an antimicrobial effect. It is particularly effective against *Staphylococcus epidermidis*. As described above, this pathogen is usually found on the skin of humans and, presumably for this reason, is in many cases the cause of post-implantation infection. Studies indicate that, in particular in the spinal region, there is an increased risk of this pathogen causing an infection after implantation. This is possibly aided by the fact that *Staphylococcus epidermidis* has a comparatively low virulence among staphylococci. This leads to the signs of infection appearing later and thus possibly being overlooked at first. Since the coating is effective against precisely this pathogen, in particular an infection that is often detected very late for the aforementioned reason can be prevented.

The at % content of silver is preferably lower than the at % content of titanium. In other words, it is not necessary for there to be a stoichiometric distribution. The distribution may be hyperstoichiometric or substoichiometric. In total, the coating comprises a content of at least 70 at-% titanium nitride.

A maximum silver content of 30 at % ensures that the titanium nitride comprises deposits of silver or silver islands and not vice versa. This has the advantage that the titanium nitride provides an essentially continuous coating, in which the silver is embedded. A dissolving out of silver therefore generally has no negative influence on the functionality of the coating. As already described above, this even tends to extend the antimicrobial range of protection.

Other preferred silver contents for the present coating, such as a silver content of 5 to 20 at %, 8 to 15 at %, 8 to 10 at % or approximately 10 at %, also have this advantage. This structure of the coating inter alia leads to at least part of the silver content being present on the coating surface in addition to the titanium nitride content.

In addition to the aforementioned anti-microbial effect, the silver content, together with the ceramic titanium nitride content as a titanium nitride/silver coating, also leads to a change in the mechanical properties as compared to a pure titanium nitride coating. This structure in particular makes the coating softer.

It is presumed that owing to the ductility associated therewith, its mechanical resistance or strength is still sufficient to withstand the mechanical influences that occur during implantation of the implant. Such mechanical influences occur, for example, when creating a press fit of an implant in the bone tissue, through contact of an implant component with a fastening element, such as, for instance, when screwing in bone screws to fix a plate, or during assembly with another implant component, such as in a spondylodesis structure.

For this reason, the present coating is suitable in particular for implants which support the skeleton of a patient after implantation or replace parts of this skeleton. In the case of such implants, mechanical stress on the coating generally occurs during implantation and assembly of an implant. After implantation tensions and extensions occur in the coating in particular owing to the everyday stress on the implant in a patient's body. The present coating is advantageous here too.

In other words, the coating is particularly suitable for implants in which abrasion primarily occurs during implantation and/or assembly of the implant. In other words, the coating essentially does not suffer any function-related abrasion in the implanted state. It was found that a thickness of the coating of less than 10 µm, in particular of 2.5 to 6 µm, preferably 3.5 to 5.5 µm and even more preferably approximately 4.5 µm, is sufficient herefor. However, it is also conceivable to use such a coating with a higher layer thickness. This can, for example, be advantageous when using this coating on the joint surfaces of a joint implant.

Furthermore, in the present coating, the difference in material properties, in particular the elasticity, as compared to the underlying base material of the implant can sometimes be lower owing to the silver content. This also ensures sufficient mechanical resistance and adhesion of the coating. For inter alia this reason, the coating can also be applied to a wide variety of different implant materials.

In summary, the titanium nitride/silver layer of the coating thus exhibits both advantageous anti-microbial and mechanical properties that are useful for an implant coated with this coating at least in sections.

Such a coating is preferably produced using the physical vapour deposition (PVD) process mentioned above. Before being inserted into the coating chamber, the implant to be provided with the coating is cleaned with water.

The implant is then inserted into the coating chamber, which is then evacuated. For the subsequent processes, the implant is preferably heated to 400 to 600° C. in order to improve the mobility of ions on the surface of the implant and to achieve better adhesion of the coating on the implant.

Further cleaning of the implant surface is preferably carried out inside the coating chamber and before the coating is applied. For example, cleaning can be carried out by means of a glow discharge in a hydrogen atmosphere in order to remove any organic residues on the uncoated implant surface.

It is furthermore possible to carry out cleaning of the implant surface by means of ion etching. The implant is hereby bombarded with ions (for example titanium ions, argon ions) under an inert atmosphere, in particular an argon atmosphere, in order to remove an oxide layer that may be present on the surface of the uncoated implant material. This also results in a better adhesion of the coating to the surface of the implant.

The cited cleaning steps preferably take place in a vacuum atmosphere of $10^{-1}$ to $10^{-4}$ mbar.

After this optional cleaning, the coating is applied to the implant under a nitrogen atmosphere.

As already described above, this coating can be realised according to its desired composition with at least one silver target and at least one titanium target. It is also possible to use one or more targets that comprise the at % contents of silver and titanium intended for the coating. The composition of the coating is hereby consequently determined by the composition of the at least one target.

In order to keep a scattering of the evaporated target material on gas particles in the coating chamber and thus the loss of target material as low as possible, the coating is carried out under a vacuum in a range of $10^{-2}$ to $10^{-3}$ mbar.

Once the desired atmosphere has been set, the evaporation process of the at least one target begins. An arc is particularly preferred for this purpose, which removes material from the targets by means of electrical discharge using a strong current and transfers it to the gas phase. During this discharge, voltages in a range of 15 to 30 V and preferably in a range of 20 to 25 V, and currents in a range of 40 to 70 A are in particular used. However, the person skilled in the art understands that other methods can also be used for evaporating the targets, such as thermal evaporation, electron beam evaporation or laser evaporation.

At least during part of the coating process, coating with the silver target and the titanium target occurs simultaneously when using targets with different materials in order to produce the titanium nitride/silver coating structure described above.

Depending on the base material of the implant to be coated, a negative voltage of 100 V to 1500 V can also be applied thereto in order to improve adhesion and layer homogeneity. In order to achieve the most uniform coating possible, the targets and the implant can also be moved relative to one another during the coating process.

Following coating and a cooling phase, the coating chamber is ventilated again and the coated implant or implants can be removed. Cooling is preferably carried out with the support of a gas atmosphere (for example nitrogen or an inert gas) for improved heat dissipation such that the cooling process is accelerated.

The invention claimed is:

1. Coating for an implant component, the coating comprising a ceramic titanium nitride coating comprising an at % content of 5 to 30 at % of Ag, wherein the Ag is Ag agglomerates in a range of 5 μm to 30 μm, wherein a surface of the coated section comprises titanium nitride with Ag agglomerates embedded therein, wherein at least a portion of the Ag agglomerates are exposed on the surface of the coating.

2. The coating according to claim 1, wherein said coating comprises 5 to 20 at % of Ag.

3. The coating according to claim 1, wherein said coating has a thickness of 2.5 to 6 μm.

4. The coating according to claim 1, in which the titanium nitride coating is essentially a stoichiometric TiN layer.

5. Implant component, which is coated at least in sections with a coating according to claim 1.

6. The implant component according to claim 5, wherein said implant component is at least one component of a spondylodesis implant or a cage.

7. The implant component according to claim 1, wherein said implant comprises a titanium alloy.

8. Method for applying an implant coating according to claim 1 to an implant component, comprising the steps of:
Providing an implant component to be coated in a coating chamber;
Providing at least one target having an at % content of silver and titanium that is predetermined for coating and/or providing at least one Ti target and at least one Ag target;
Providing an atmosphere containing at least nitrogen;
Evaporating the at least one target; and
Simultaneously coating the implant component with the evaporated metal of the at least one target.

9. The method for applying an implant coating according to claim 8, wherein the evaporation of the at least one target is carried out by means of arc evaporation and the voltage applied to the targets is 15 to 30 V or 20 to 25 V, and the applied current is 40 to 70 A.

10. The method according to claim 8, in which, once the implant to be coated has been provided in the coating chamber, the implant surface to be coated is cleaned by a glow discharge under a hydrogen atmosphere.

11. The method according to claim 8, in which, once the implant to be coated has been introduced into the coating chamber, the implant surface to be coated is cleaned by bombarding the implant surface with ions under an inert atmosphere.

12. Use of the coating according to claim 1 for preventing a biofilm on an implant.

13. The coating according to claim 1, wherein the implant component is a spinal implant.

14. The implant component according to claim 5, wherein the implant component is a spinal implant.

15. The coating according to claim 1, wherein the at % content of silver is lower than an at % content of titanium.

16. The coating according to claim 1, wherein said coating comprises 8 to 15 at % of Ag.

17. The coating according to claim 1, wherein said coating comprises approximately 10 at % of Ag.

18. The coating according to claim 1, wherein said coating has a thickness of 3.5 to 5.5 μm.

19. The implant component according to claim 5, wherein no oxide layer is present on a surface of the implant, between the surface of the implant and the coating.

20. The coating according to claim 1, wherein, the coating is applied by an evaporation process, wherein the evaporation process comprises applying an arc evaporation voltage to at least one target comprising Ti and Ag, wherein the arc evaporation voltage is 15 V to 30 V.

* * * * *